(12) United States Patent
Yurke

(10) Patent No.: US 12,173,027 B2
(45) Date of Patent: Dec. 24, 2024

(54) EXCITONIC QUANTUM COMPUTING MEDIATED BY CHROMOPHORE-EMBEDDED 1-, 2-, AND 3-DIMENSIONAL DNA SCAFFOLDS

(71) Applicant: BOISE STATE UNIVERSITY, Boise, ID (US)

(72) Inventor: Bernard Yurke, Boise, ID (US)

(73) Assignee: Boise State University, Boise, ID (US)

( * ) Notice: Subject to any disclaimer, the term of this patent is extended or adjusted under 35 U.S.C. 154(b) by 1402 days.

(21) Appl. No.: 16/100,052

(22) Filed: Aug. 9, 2018

(65) Prior Publication Data

US 2019/0048036 A1 Feb. 14, 2019

Related U.S. Application Data

(60) Provisional application No. 62/543,051, filed on Aug. 9, 2017.

(51) Int. Cl.

| C07H 21/04 | (2006.01) |
| C07H 21/02 | (2006.01) |
| C09B 11/08 | (2006.01) |
| C09B 23/06 | (2006.01) |
| C09B 23/08 | (2006.01) |
| G06N 3/123 | (2023.01) |
| G06N 10/00 | (2022.01) |

(52) U.S. Cl.
CPC ............. *C07H 21/04* (2013.01); *C07H 21/02* (2013.01); *C09B 11/08* (2013.01); *C09B 23/06* (2013.01); *C09B 23/083* (2013.01); *G06N 3/123* (2013.01); *G06N 10/00* (2019.01)

(58) Field of Classification Search
CPC ......... C07H 21/04; C07H 21/02; C09B 11/08; C09B 23/06; C09B 23/083; G06N 3/123; G06N 10/00
See application file for complete search history.

(56) References Cited

U.S. PATENT DOCUMENTS

| 9,073,962 B2 | 7/2015 | Fracchia et al. |
| 2004/0209355 A1* | 10/2004 | Edman .................. C12M 35/02 |
| | | 257/E21.705 |
| 2015/0218204 A1 | 8/2015 | Yin et al. |

(Continued)

FOREIGN PATENT DOCUMENTS

WO 2014018675 A1 1/2014

OTHER PUBLICATIONS

Cannon et al. (ACS Photonics, 2015, 2, pp. 398-404). (Year: 2015).*

(Continued)

*Primary Examiner* — Jezia Riley
(74) *Attorney, Agent, or Firm* — McKee, Voorhees & Sease, PLC

(57) ABSTRACT

Using nucleotide architectures to very closely and precisely placed chromophores that produce quantum coherent excitons, biexcitons, and triexcitons upon excitement to create excitonic quantum wires, switching, and gates that would then form the basis of quantum computation. Creating the various excitons and controlling the timing of the excitons would be performed using light of the corresponding wavelength and polarization to stimulate the corresponding chromophores.

30 Claims, 12 Drawing Sheets

(56) References Cited

U.S. PATENT DOCUMENTS

2017/0190573 A1 7/2017 Shen et al.
2018/0044372 A1 2/2018 Han et al.

OTHER PUBLICATIONS

Graugnard et al. Nano Lett. 2012, 12, 2117-2122 with Supporting Information. (Year: 2012).*
Spillmann et al. (Journal of Photochemistry and Photobiology C: Photochemistry Reviews 23 (2015) 1-24). (Year: 2015).*
Cannon et al., "Coherent Exciton Delocalization in a Two-State DNA-Templated Dye Aggregate System", Journal of Physical Chemistry, vol. 121, pp. 6905-6916, Aug. 16, 2017.
Cannon et al., "Large Davydov Splitting and Strong Fluorescence Suppression: An Investigation of Exciton Delocalization in DNA-Templated Holliday Junction Dye Aggregates", Journal of Physical Chemistry, vol. 122, pp. 2086-2095, Feb. 8, 2018.
Cannon et al., "Large Davydov Splitting and Strong Fluorescence Suppression: An Investigation of Exciton Delocalization in DNA-Templated Holliday Junction Dye Aggregates", Supporting Information, 20 pages, Feb. 8, 2018.
Childs et al., "Universal Computation by Multiparticle Quantum Walk", Science Mag., vol. 339, pp. 791-794, Feb. 15, 2013.
Ke et al., "Three-Dimensional Structures Self-Assembled from DNA Bricks", Science, vol. 338(6111), 16 pages, Nov. 30, 2012.
Wei et al., "Complex shapes self-assembled from single-stranded DNA tiles", Nature, vol. 485, pp. 623-627, May 31, 2012.
Yurke et al., "Passive linear nanoscale optical and molecular electronics device synthesis from nanoparticles", Physical Review, vol. A81, 9 pages, 2010.
Castellanos et al., "On the Design of Molecular Excitonic Circuits for Quantum Computing: The Universal Quantum Gates", Phys. Chem. Chem. Phys., vol. 22, pp. 3048-3057, 2020.
Rothemund, Paul W. K., "Folding DNA to create nanoscale shapes and patterns", Nature, vol. 440, pp. 297-302, 2006.

* cited by examiner

EXCITONIC QUANTUM COMPUTING MEDIATED BY CHROMOPHORE-EMBEDDED 1-, 2-, AND 3-DIMENSIONAL DNA SCAFFOLDS

CROSS REFERENCE TO RELATED APPLICATION

The present application claims priority to the earlier filed U.S. Provisional application having Ser. No. 62/543,051, filed Aug. 9, 2017 and hereby incorporates subject matter of the provisional application in its entirety.

GRANT REFERENCE

This invention was made with government support under Grant No. NNX15AI04H, awarded by the National Aeronautics and Space Administration, and Grant No. ECCS-1014922, awarded by the National Science Foundation. The Government has certain rights in the invention.

FILED OF THE INVENTION

The invention relates generally to quantum computing. More specifically, the invention relates to chromophores bound to a nucleotide oligomer architecture, which are used to propagate excitons down wires or through gates for use in quantum calculations.

BACKGROUND OF THE INVENTION

An exciton is the name for the energy packet that resides on a chromophore when it is in its excited state. When two molecules are very close to each other the energy of an excited chromophore can be transferred to a neighboring chromophore without energy loss, in contrast to the usual fluorescence resonance energy transfer (FRET) where energy loss occurs in the transfer. The packet of energy can be exchanged in a wave like manner back and forth between the two molecules. The energy packet, in this sense, acts like a quantum mechanical particle that can become delocalized or spread out over an aggregate of chromophores just like an electron can spread out its wave function over an entire molecule (molecular orbital). The Davydov splitting and the circular dichroism (CD) spectra seen in chromophore aggregates is a manifestation of this delocalization. Davydov splitting is analogous to the splitting of orbitals into bonding and antibonding orbitals when two atoms are brought close together.

Exciton wires can be made by closely spacing chromophores together in a row. As discussed above, when chromophores are nanospaced apart, an exciton may transfer from one chromophore to another without the loss of energy. An exciton created at one end of the row of chromophores may propagate down the row, hopping from one chromophore nanospaced to the next. This is done in a wavelike manner.

Exciton circuits made from these exciton wires may be made to be analogous to electronic circuits but where excitons carry the signals rather than electrons in classical computing. By bringing two exciton wires sufficiently close to each other an exciton can hop from one wire to the other by transferring from one chromophore to another. By doing this carefully one can make devices that function as signal dividers such as those found in Yurke and Kuang (*Passive linear nanoscale optical and molecular electronics device synthesis from nanoparticles,* 2000, Phys. Rev. A, 81, 033814, herein incorporated by reference). The division ratio depends on rates with which excitons can be transferred between chromophores in the coupling region. The transfer rate depends on the spacing between the chromophores, their orientations. This dependence on spacing and orientation enables the construction of signal dividers with, for practical purposes, any division ratio. An exciton propagating down one exciton wire will become delocalized so that one must think of the exciton as being in a superposition state where it resides on both exciton wires. This device is a basis-change gate. Its function is analogous to that of an optical beam splitter or microwave directional coupler. A basis-change gate is one of the fundamental quantum gates.

Another quantum gate of fundamental importance is a phase-shift gate. The phase accumulated by an exciton is proportional to the distance it travels. Hence, a phase-shift gate can simply be made by engineering the wire that the exciton travels over to have the length needed to accumulate the proper amount of phase. The phase an exciton accumulates is also determined by its energy relative to the optical transition energy for the chromophore. The optical transition frequency here denotes the energy difference between the chromophore's ground electronic state and its lowest excited electronic state that has an allowed optical transition. Hence, phase shifters can also be fashioned choosing the chromophores of differing optical transition energies. It is also possible to make phase shifters by terminating two ports of a signal divider with chromophores having differing optical transition energies as shown by Yurke and Kuang (2010).

Another quantum gate of fundamental importance is a controlled basis change gate. In contrast to the gates already discussed, which rely on wave interference effects, a controlled basis change gate relies on the interaction between two excitons. When two excitons reside on neighboring chromophores they feel each other's presence just like two electrons will feel each other's Coulomb repulsion when they are brought close together. The two exciton interaction arises from static Coulomb interactions between molecules and is most strong when the molecules have an asymmetric molecular structure. Asymmetric molecules possess a permanent electric dipole which changes sign when the molecule is excited from the ground state to the excited state. The static Coulomb interaction, in this case is a dipole-dipole interaction which, when both chromophores are excited (the two exciton case), differs in sign from the case when only one chromophore is excited (the one exciton case). Due to the static Coulomb interactions between chromophores one exciton will accumulate extra phase in the presence of the other exciton. As a result, the presence or absence of one exciton can control how the other exciton moves through a basis change gate.

These three types of gates, the basis-change gate, the phase-shift gate, and the controlled basis-change gate, form a complete set if the phase-shift gates can be produces with a finite set of phase angles. Since the phase angles can be controlled by the exciton path length, the optical transition energies of the phase-shifter wire chromophores or through the construction of optical phase-shifter gates out of basis-change gates with selected ports terminated this last requirement can be met. With this finite set of gates, one can assemble exciton circuits that perform any quantum computation. A set of gates having this property is said to be capable of universal quantum computation. This is analogous to the electronic computer case where the NAND gate is a universal gate in that any Boolean function can be implemented by a circuit employing only NAND gates.

It is possible to perform universal quantum computation with just basis-change gates and phase-shift gates, but the number of parts (gates) one needs grows exponentially with the size of the problem. So, doing quantum computation this way performs as well as classical computers. By introducing basis-change gates one can drastically reduce the parts count so that much fewer parts are required than for a classical computer. The controlled basis-change gate enables the entanglement of many-body (many-exciton) states so that a network of quantum gates acts as if it is performing many different computations simultaneously. This is similar to an n bit memory register. In a classical computer each memory element of the register can be in either a zero or a one state but not both simultaneously. In contrast a quantum mechanical register can be in a state that is a quantum mechanical superposition of being in the zero state and the one state. An n bit quantum memory in this sense can act as if it is holding 2n bits of information whereas the classical computer memory only holds n bits of information. A single controlled basis change gate excepting as inputs the contents of memory elements i and j and delivering the outputs back to memory elements i and j can update the amplitudes of all of the 2n states in the superposition of the memory register simultaneously. This is quantum parallelism.

Not all math problems are known to benefit from quantum speedup, but several classes of problems are known where quantum computers can vastly outperform classical computers. Two of the problems are factoring and database searching.

However, chromophores exhibit many non-ideal characteristics for quantum computing. The electronic degrees of freedom are strongly coupled to the vibrational and environmental degrees of freedom. This causes phase jitter, which causes phase error to grow with time, thus spoiling the interference effects that the quantum gates relay on. All quantum computers suffer from this problem to a greater or lesser extent. Chromophores are also difficult to arrange in the requisite configurations.

What exciton quantum computers have in their favor is fast switching time, compact size (the components are relatively small molecules), and possible room temperature operation. Since photons are readily converted into excitons and excitons are readily converted into photons, it is noted that the above excitonic devices may find application in optical information processing, apart from quantum computing, as more compact embodiments of the currently employed optical phase shifters, signal dividers, and switches, employing Kerr nonlinearities, that have the functionality of controlled basis change gates. For these applications the performance requirements are less demanding than that for quantum computation.

BRIEF SUMMARY OF THE INVENTION

Applicants have created compositions of one or more chromophores attached to a nucleotide architecture. When two or more chromophores are spaced close enough in which an exciton is transferred from one chromophore to another without energy loss (nanospaced) within the nucleotide architecture they can propagate excitons down quantum wires and through quantum circuits, which can be used in quantum computing. The use of chromophores in quantum computing has several benefits over traditional methods, including functioning in a noisy environment and being able to be performed at room temperatures. The use of the nucleotide architecture allows for self-assembly of complex structures which place the chromophores in precise locations as well as placing the chromophores sufficiently close to each other to allow for the transfer of excitons without energy loss. Further, the use of nucleotides has benefits over the use of proteins for an architecture due to having less complex design rules.

In an embodiment, chromophores are attached to a nucleotide architecture to make exciton wires. In further embodiments, the nucleotide architecture configures the exciton wires into gates or switches. These gates or switches include, but are not limited to, basis gates, phase gates, controlled basis gates, Hadamard gates, momentum switches, and CO gates. In yet further embodiments, the switches and gates are configured into exciton circuits. These wires, gates, switches, and circuits can then be used in quantum computing to solve mathematical problems, as well as sorting and querying problems.

In other embodiments, to answer a problem being calculated by a quantum circuit, the exciton wires are initialization by exciting only a subset of the chromophores, the input chromophores, to start the propagation of excitons through the rest of the chromophores within the quantum circuit. In further embodiments the chromophore orientations are chosen and exposed to polarized light in such a manner that only the desired subset of chromophores is excited when the system is hit with an initializing pulse of light. In other embodiments, the input chromophores are initialized by lasers. In some embodiments, the readout of the circuit, containing the results of the calculation, can be done by using fluorescent reporter dyes delivered by fluorescent resonance energy transfer (FRET).

In the embodiments the nucleotide architecture is self-assembling. In some embodiments, the nucleotide architecture is double stranded. In yet other embodiments, the nucleotide architecture is single stranded. In another embodiment, to allow the attachment of additional chromophores when compared to a single stranded architecture, the nucleotide architecture is double stranded. In some embodiments the nucleotide architecture is linear for fast transmission speed down a wire or to allow fine tuning by reagents. In other embodiments the nucleotide architecture is two- or three-dimensional to allow for more complex circuits or to increase rigidity of the chromophores within the architecture. In other embodiments the nucleotide strands comprising the architecture may be branched to allow for increased complexity of the structure. In further embodiments, the nucleotide strands are configured by nucleotide origami. In other further embodiments, the nucleotide strands are configured into nucleotide bricks allowing for very complex and controlled three-dimensional structures.

While multiple embodiments are disclosed, still other embodiments of the present invention will become apparent to those skilled in the art from the following detailed descriptions, which show and describe illustrative embodiments of the invention. Accordingly, the figures and detailed description are to be regarded as illustrative in nature and not restrictive.

BRIEF DESCRIPTION OF THE DRAWINGS

FIGS. 1A-1C show the chromophore bound to the same nucleotide duplex.

FIG. 7A is a schematic representation of a phase gate, representing a phase shifter consisting of a modified 50:50 beam splitter with two detuned nanoparticles, labeled # and *. The phase shifter is a two-port network derived from the 50:50 beam splitter, shown in FIG. 7B, by replacing the transmission lines of ports 3 and 4 with two chromophores whose resonant frequency is slightly detuned from the rest of the chromophore circuit. The relative coupling strength between the adjacent chromophores is labeled on the corresponding link. FIG. 7B is a schematic representation of a basis-changing gate where the device nodes are labeled with the integers 1 through 4. The transmission line nodes are indicated by pairs of numbers r, m where the first labels the transmission line and the second labels a node along that transmission line. The hopping interaction coupling strengths between pairs of nodes within the device are labeled by $g_n$, where n is 1 or 2. The hopping interaction coupling strengths between neighboring nodes along the transmission lines are all taken to be equal to g. The direction of propagation of the incoming $a_r^{in}$ and outgoing $a_r^{out}$ amplitudes for each of the transmission lines is also indicated. FIG. 7C is a schematic representation of a controlled basis change gate with a phase shifting element between two basis change gates.

DETAILED DESCRIPTION

Figure 1A:
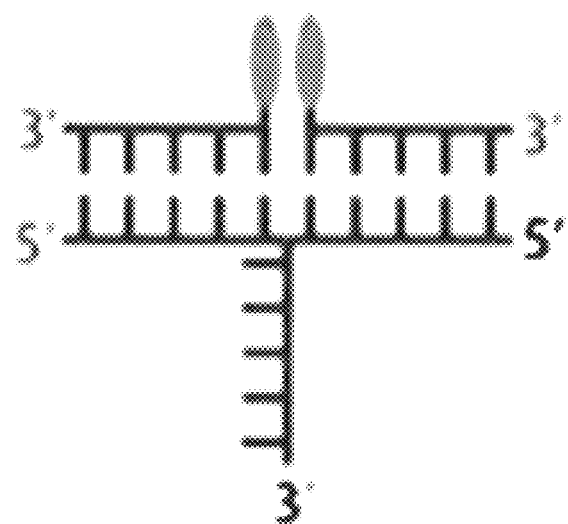
FIG. 1A is a schematic representation of a simple three-way branched nucleotide brick bringing together two other bricks with the chromophore bound to their 5' ends.

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. The methods and techniques are generally performed according to conventional methods well known in the art and as described in various general and more specific references that are cited and discussed throughout the present specification unless otherwise indicated.

Definitions

The following terms, unless otherwise indicated, shall be understood to have the following meanings:

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Other than in the operating examples, or where otherwise indicated, all numbers expressing quantities of ingredients or reaction conditions used herein are to be understood as being modified in all instances by the term "about".

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

"Non-covalent" refers to any molecular interactions that are not covalent—i.e. the interaction does not involve the sharing of electrons. The term includes, for example, electrostatic, π-effects, van der Waals forces, and hydrophobic effects. "Covalent" refers to interactions involving the sharing of one or more electrons.

As used herein, a "brick" is a structural unit. A brick may be of any shape or size. The main body of a brick may be of any material composition. An example of a brick is a "nucleotide brick," which is a structural unit where the body of the brick is made of a nucleotide oligomer. An example of a nucleotide brick is a "DNA brick," which is a nucleotide brick where the body of the brick is made of a DNA oligomer.

As used herein, a "nucleotide" is any nucleoside linked to a phosphate group. The nucleoside may be natural, including but not limited to, any of cytidine, uridine, adenosine, guanosine, thymidine, inosine (hypoxanthine), or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, which act as a linker group lacking a base or be a nucleotide analog.

As used herein, "nucleotide duplex" is when two strands of complement nucleotide oligomers complementary bind to each other. The two strands may be part of the same nucleotide molecule or separate nucleotide molecules.

As used herein, "nucleotide origami" is two or more nucleotide bricks, where one brick is a "scaffold" and provides the main body of the overall structure and is bound by one or more "staple(s)."

As used herein, a "scaffold" is a single stranded nucleotide brick rationally-designed to self-assemble into hairpin loops, helical domains, and locking domains. The scaffold may use staples to direct the folding and to hold the final shape. Alternatively, the scaffold may use intrinsic self-complementary pairing to hold the final shape.

As used herein, a "staple" or "staple strand" is a nucleotide brick which pairs with a longer main body brick in nucleotide origami to help fold the main body brick into the desired shape.

As used herein, a "nanobreadboard," "breadboard," or "template" is a total or final structure of a DNA structure or shape. For example, a mobile or immobile 4-arm junction, DNA origami happy face, rectangular brick, or double stranded DNA (dsDNA) in its final structure.

As used herein, an "architecture" is a one-, two-, or three-dimensional structure built using one or more bricks. As used herein, a "nucleotide architecture" is a one-, two-, or three-dimensional structure built using one or more nucleotide bricks. Examples include nucleotide origami or molecular canvases.

As used herein, "self-assembly" refers to the ability of nucleotides to anneal to each other, in a sequence-specific manner, in a predicted manner and without external control.

As used herein, "sufficiently close" and "nanospaced" refers to a distance between two chromophores that allows one chromophore, when excited, to emit an exciton and transfer the exciton to a second chromophore without a loss of energy.

As used herein, a "breadboard" refers to reusable solderless device used to build an exitonic circuit. The breadboard allows for temporary placement of different solutions, such as solutions containing chromophore bound nucleotide architectures, in different arrangements.

Nucleotide Architecture

Nucleotide nanotechnology can be used to form complicated one-, two-, and three-dimensional architectures. The nucleotide architectures may comprise of one or more nucleotide bricks. The nucleotide bricks are designed to use the Watson-Crick pairing of the nucleotides to cause the bricks to self-assemble into the final and predictable architectures. Any method of designing the architectures and self-assembly may be used, such as but not limited to nucleotide origami, nucleotide brick molecular canvases, single stranded tile techniques, or any other method of nucleotide folding or nanoassembly such as, but not limited to, using nucleotide tiles, nucleotide scaffolds, nucleotide lattices, four-armed junction, double-crossover structures, nanotubes, static nucleotide structures, dynamically changeable nucleotide structures, or any other synthetic biology technique (as described in U.S. Pat. No. 9,073,962, U.S. Pub. No.: US 2017/0190573, U.S. Pub. No.: US 2015/0218204, U.S. Pub. No.: US 2018/0044372, or International Publication Number WO 2014/018675, each of which is incorporated by reference).

The nucleobase making up the bricks may be natural, including but not limited to, any of cytosine, uracil, adenine, guanine, thymine, hypoxanthine, or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, or alternatively a nucleotide analog may be used.

Non-limiting examples of synthetic nucleobases and analogs include, but are not limited to methyl-substituted phenyl analogs, such as but not limited to mono-, di-, tri-, or tatramethylated benzene analogs; hydrophobic base analogs, such as but not limited to 7-propynyl isocarbostyril nucleoside, isocarbostyril nucleoside, 3-methylnapthalene, azaindole, bromo phenyl derivates at positions 2, 3, and 4, cyano derivates at positions 2, 3, and 4, and fluoro derivates at position 2 and 3; purine/pyrimidine mimics, such as but not limited to azole hetercyclic carboxamides, such as but not limited to (1H)-1,2,3-triazole-4-carboxamide, 1,2,4-triazole-3-carboxamide, 1,2,3-triazole-4-carboxamide, or 1,2-pyrazole-3-carboxamide, or heteroatom-containing purine mimics, such as furo or theino pyridiones, such as but not limited to furo[2,3-c]pyridin-7(6H)-one, thieno[2,3-c]pyridin-7(6H)-one, furo[2,3-c]pyridin-7-thiol, furo[3,2-c]pyridin-4(5H)-one, thieno[3,2-c]pyridin-4(5H)-one, or furo[3,2-c]pyridin-4-thiol, or other mimics, such as but not limited to 5-phenyl-indolyl, 5-nitro-indolyl, 5-fluoro, 5-amino, 4-methylbenzimidazole, 6H,8H-3,4-dihydropropyrimido[4,5-c][1,2]oxazin-7-one, or $N^6$-methoxy-2,6-diaminopurine; isocytosine, isoquanosine; thymidine analogs, such as but not limited to 5-methylisocytosine, difluorotoluene, 3-toluene-1-β-D-deoxyriboside, 2,4-difluoro-5-toluene-1-β-D-deoxyriboside, 2,4-dichloro-5-toluene-1-β-D-deoxyriboside, 2,4-dibromo-5-toluene-1-β-D-deoxyriboside, 2,4-diiodo-5-toluene-1-β-D-deoxyriboside, 2-thiothymidine, 4-Se-thymidine; or fluorescent base analogs, such as but not limited to 2-aminopurine, 1,3-diaza-2-oxophenothiazine, 1,3-diaza-2-oxophenoxazine, pyrrolo-dC and derivatives, 3-MI, 6-MI, 6-MAP, or furan-modified bases.

Non-limiting examples of nucleotide analogs include, but are not limited to, phosporothioate nucleotides, 2'-O-methyl ribonucleotides, 2'-O-methoxy-ethyl ribonucleotides, peptide nucleotides, N3'-P5' phosphoroamidate, 2'-fluoro-arabino nucleotides, locked nucleotides, morpholino phosphoroamidate, cyclohexene nucleotides, tricyclo-deoxynucleotides, or triazole-linked nucleotides.

The nucleotides can then be polymerized into oligomers. The design of the oligomers will depend on the design of the final architecture. Simple architectures may be designed by any methods. However, more complex architectures may be design using software such as, but not limited to, caDNAno (as described at http://cadnano.org/docs.html, and herein incorporated by reference), to minimize errors and time. The user may input the desired shape of the architecture into the software and once finalized, the software will provide the oligomer sequences of the bricks to create the desired architecture.

In some embodiments the architecture is comprised of nucleotide brick molecular canvases, wherein the canvases are made of 1 to 5,000 nucleotide bricks comprising of nucleotide oligomers of 24 to 48 nucleotides and will self-assemble in a single reaction, a "single-pot" synthesis, as described in U.S. Pub. No.: US 2015/0218204. In more preferable embodiments, the canvases are made of 1 to 1,000 nucleotide bricks, from 1 to 750 nucleotide bricks, from 1 to 500 nucleotide bricks, or from 1 to 250 nucleotide bricks. In other embodiments, the oligomers comprise of 24 to 42 nucleotides, from 24 to 36 nucleotides, or from 26 to 36 nucleotides.

In another embodiment the architecture is made step wise using a serial fluidic flow to build the final shape as described in U.S. Pat. No. 9,073,962.

In some embodiments, the architecture is assembled using the origami approach. With a DNA origami approach, for example, a long scaffold nucleic acid strand is folded to a predesigned shape through interactions with relatively shorter staple strands. Thus, in some embodiments, a single-stranded nucleic acid for assembly of a nucleic acid nanostructure has a length of at least 500 base pairs, at least 1 kilobase, at least 2 kilobases, at least 3 kilobases, at least 4 kilobases, at least 5 kilobases, at least 6 kilobases, at least 7 kilobases, at least 8 kilobases, at least 9 kilobases, or at least 10 kilobases. In some embodiments, a single-stranded nucleic acid for assembly of a nucleic acid nanostructure has a length of 500 base pairs to 10 kilobases, or more. In some embodiments, a single-stranded nucleic acid for assembly of a nucleic acid nanostructure has a length of 7 to 8 kilobases. In some embodiments, a single-stranded nucleic acid for assembly of a nucleic acid nanostructure comprises the M13 viral genome. In some embodiments the number of staple strands is less than about 500 staple strands, less than about 400 staple strands, less than about 300 staple strands, less than about 200 staple strands, or less than about 100 staple strands.

In some embodiments, the architecture is assembled from single-stranded tiles (SSTs) (see, e.g., Wei B. et al. Nature 485: 626, 2012, incorporated by reference herein) or nucleic acid "bricks" (see, e.g., Ke Y. et al. Science 388:1177, 2012; International Publication Number WO 2014/018675 A1 each of which is incorporated by reference herein). For example, single-stranded 2- or 4-domain oligonucleotides self-assemble, through sequence-specific annealing, into two- and/or three-dimensional nanostructures in a predetermined (e.g., predicted) manner. As a result, the position of each oligonucleotide in the nanostructure is known. In this way, a nucleic acid nanostructure may be modified, for example, by adding, removing or replacing oligonucleotides at particular positions. The nanostructure may also be modified, for example, by attachment of moieties, at particular positions. This may be accomplished by using a modified oligonucleotide as a starting material or by modifying a particular oligonucleotide after the nanostructure is formed. Therefore, knowing the position of each of the starting oligonucleotides in the resultant nanostructure provides addressability to the nanostructure.

In some embodiments, the architecture is made from a single stranded oligomer, as described in U.S. Pub. No.: 2018/0044372 and herein incorporated by reference. A single strand of DNA used for assembling a nanostructure in accordance with the present disclosure may vary in length. In some embodiments, a single strand of DNA has a length of 500 nucleotides to 10,000 nucleotides, or more. For example, a single strand of DNA may have a length of 500 to 9000 nucleotides, 500 to 8000 nucleotides, 500 to 7000 nucleotides, 500 to 6000 nucleotides, 500 to 5000 nucleotides, 500 to 4000 nucleotides, 500 to 3000 nucleotides, 500 to 2000 nucleotides, 500 to 1000 nucleotides, 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides. In some embodiments, a single strand of DNA may have a length of at least 2000 nucleotides, at least 3000 nucleotides, at least 4000 nucleotides, or at least 5000 nucleotides. In some embodiments, a single strand of DNA may have a length of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3100, 3200, 3300, 3400, 3500, 3600, 3700, 3800, 3900, 4100, 4200, 4300, 4400, 4500, 4600, 4700, 4800, 4900, 5100, 5200, 5300, 5400, 5500, 5600, 5700, 5800, 5900, 6600, 6200, 6300, 6400, 6500, 6600, 6700, 6800, 6900, 7100, 7200, 7300, 7400, 7500, 7600, 7700, 7800, 7900, 8100, 8200, 8300, 8400, 8500, 8600, 8700, 8800, 8900, 9100, 9200, 9300, 9400, 9500, 9600, 9700, 9800, 9900, or 10000 nucleotides.

In some embodiments, the architecture is two-dimensional and comprises a single layer of bricks or a single scaffold. The single layer of bricks may form a molecular canvas. In other embodiments, the architecture is three-dimensional and may contain 2, 3, 4, 5, 6, 7, 8, 9, 10, 20, 30, or more layers of two-dimensional structures depending on the desired final shape.

In some embodiments, the architecture is attached to a substrate, such as a glass slide, a silicon base, or a breadboard.

In other embodiments, the architecture remains in a solution. By altering aspects of the solution, such as but not limited to pH, salt concentrations, and cation charge, the aggregation of the bricks may be changed, which may change the orientation, as well as the absorbance spectra, of the chromophores.

Chromophores

When chromophores aggregate in high concentrations in solution excitonic quantum coherent behavior (e.g. large Davydov splitting, exchange narrowing, circular dichroism, Cotton effects, or Stokes shifting) can be observed. When excited, the chromophore may emit an exciton, an electron and electron hole pair. If two chromophores are sufficiently close to each other, the emitted exciton may be transmitted from the excited chromophore to the neighboring chromophore without a loss in energy. Chromophore based excitonic quantum coherent effects may occur at room temperature in wet and noisy environments and the systems may be less than about 10 nm. These systems provide several large benefits over the currently available excitonic quantum coherent systems, which are much larger, measuring in the micrometer size, and required extreme operating conditions, such as cryogenic temperatures, external magnetic fields and/or large microwave pulses, and dry environments.

Any chromophore that emits an exciton when excited is acceptable may be used in any embodiment. A chromophore may be symmetrical or preferably asymmetrical. By way of non-limiting examples, the chromophore may be one or more of a commercial chromophore(s), such as but not limited to Freedom™ Dye, Alexa Fluor® Dye, LI-COR IRDyes®, ATTO™ Dyes, Rhodamine Dyes, or WellRED Dyes; or any other dye. Examples of Freedom™ Dyes include 6-FAM, 6-FAM (Fluorescein), Fluorescein dT, Cy3™ TAMRA™, JOE, Cy5™ TAMRA, MAX, TET™, Cy5.5™, ROX, TYE™ 563, Yakima Yellow®, HEX, TEX 615, TYE™ 665, TYE 705, and Dyomic Dyes. Examples of Alexa Fluor® Dyes include Alexa Fluor® 488, 532, 546, 647, 660, and 750. Examples of LI-COR IRDyes® include 5' IRDye® 700, 800, and 800CW. Examples of ATTO™ Dyes include ATTO™ 488, 532, 550, 565, Rho101, 590, 633, 647N. Examples of Rhodamine Dyes include Rhodamine Green™-X, Rhodamine Red™-X, and 5-TAMRA™. Examples of WellREd Dyes include WellRED D4, D3, and D2. Examples of Dyomic Dyes include Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, -601XL. Examples of other dyes include 6-FAM, Fluorescein, Texas Red®-X, and Lightcycler® 640.

Using the above architectures to which the chromophore are bound, two or more chromophores may be precisely placed with nanometer precision apart from each other. When so placed, the chromophores may produce quantum coherent excitons, biexcitons, and triexcitons when excited by a light source. In some exemplary embodiments, the two or more chromophores are covalently bound to the same nucleotides brick, and then the chromophore bound brick and any non-bound bricks are allowed to self-assemble into the desired final one-, two-, or three-dimensional shape. In another embodiment, the two or more chromophores are covalently bound to different nucleotide bricks and then the bricks are allowed to self-assemble into the desired final one-, two-, or three-dimensional shape.

In some embodiment, the bricks are allowed to first self-assemble into the desired final one-, two-, or three-dimensional shape. Portions of the bricks may still be unpaired after assembly, allowing for further binding of complementary oligomers. The two or more chromophores are bound to at least one complementary oligomer which may then pair with the one or more unpaired portions of the bricks.

Figure 1B:
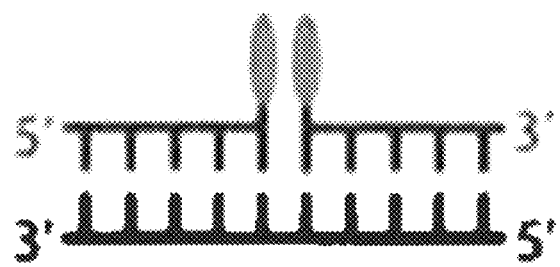
FIG. 1B is a schematic representation of a simple nucleotide brick bringing together two chromophore bound separate bricks, one with a chromophore bound to the 3' end and the other to the 5' end.
Figure 1C:
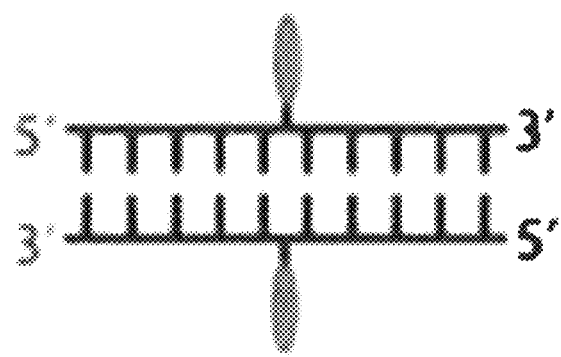
FIG. 1C is a schematic representation of two simple nucleotide bricks, either bound with a chromophore, with the chromophore bound internally in both bricks.
Figure 1D:
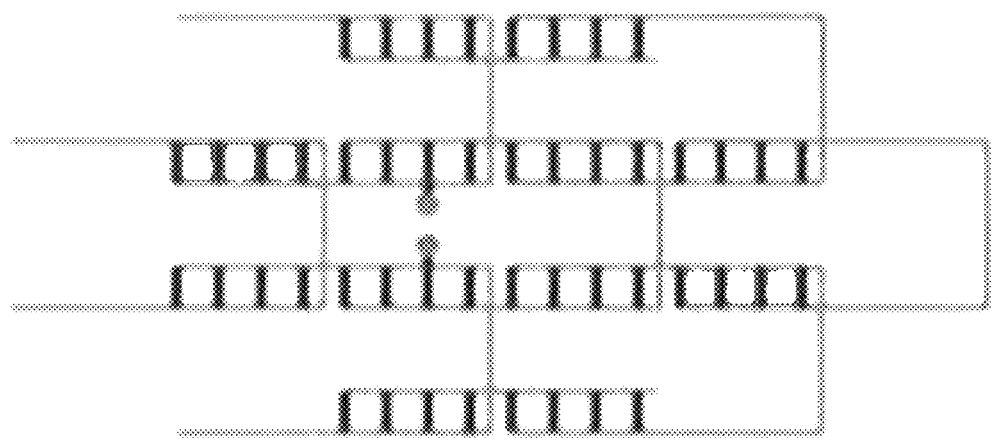
FIG. 1D is a schematic representation of a canvas with two of the bricks bound with a chromophore internally and on different nucleotide duplexes.

In some embodiments, the chromophores are bound to the 5' ends of the nucleotide bricks (FIG. 1A). In other embodiments, the chromophores are bound to the 3' ends of the nucleotide bricks. In yet other embodiments, the chromophores are bound internally within the nucleotide bricks (FIGS. 1C and 1D). In still more embodiments, the chromophores are bound to any mix of 5' ends, 3' ends, or internally (FIG. 1B). The position of the chromophore will depend on the desired final configuration. Methods of binding chromophores to nucleotides is well known in the art.

In some embodiments, the chromophores are bound to the same nucleotide duplex (FIGS. 1A-1C). In other embodiments, the chromophores are bound to separate nucleotide duplexes (FIG. 1D).

In some embodiments some of the chromophores are covalently bound to the bricks while other of the chromophores are bound to separate oligomers, and the oligomers then pair with exposed single strands of the bricks.

The orientation of the two or more chromophore dipoles to each other effect the absorbance and emission spectra. Depending on the orientation, a pair of chromophores nano-spaced apart will have different characteristics when compared to the monomer chromophore. When the dipoles are parallel an "H-dimer" forms, which are characterized by a blue-shift in absorbance due to having a higher excited energy state when compared to the monomer. When the dipoles are in a head-to-head orientation, a "J-dimer" forms, which is characterized by a red-shift in absorbance due to having a lower excited energy state when compared to a monomer. When the dipoles are at an oblique angle, a mixed "J/H-dimer" forms and is characterized by Davydov splitting due to having both a higher and lower excited energy state when compared to a monomer (see FIG. 2, and Cannon et al., *Coherent Exciton Delocalization in a Two-State DNA-Templated Dye Aggregate System*, 2017, J. Phys. Chem. A, 121: 6905-6916, herein incorporated by reference).

Figure 3A:
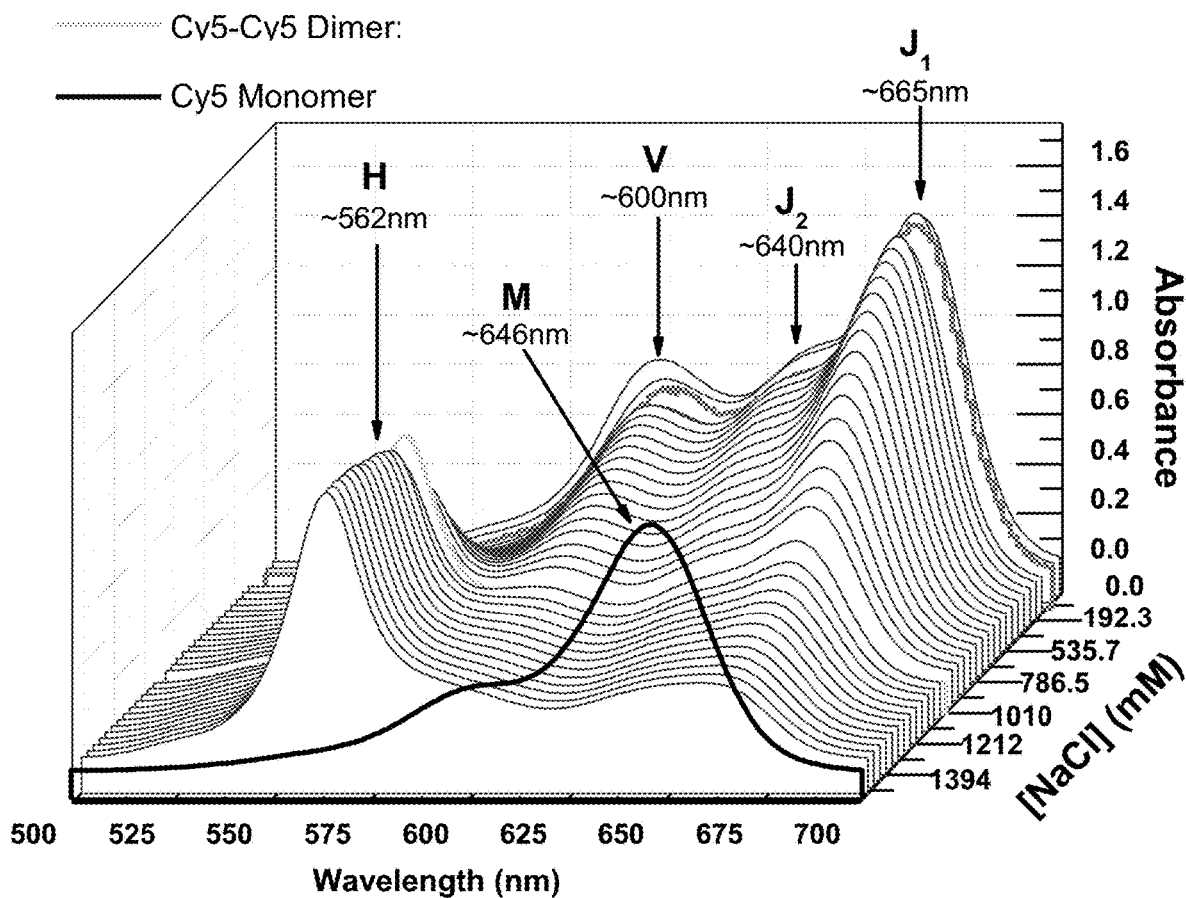
FIG. 3A is a graphical representation of changes in absorbance.
Figure 3B:
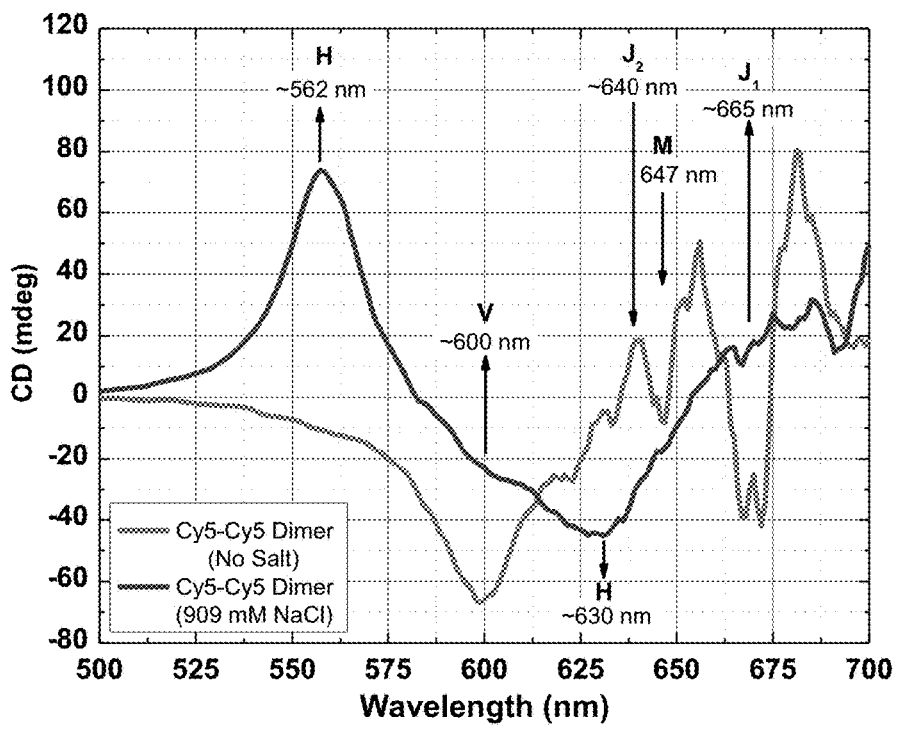
FIG. 3B is a graphical representation of circular dichroism.
Figure 3C:
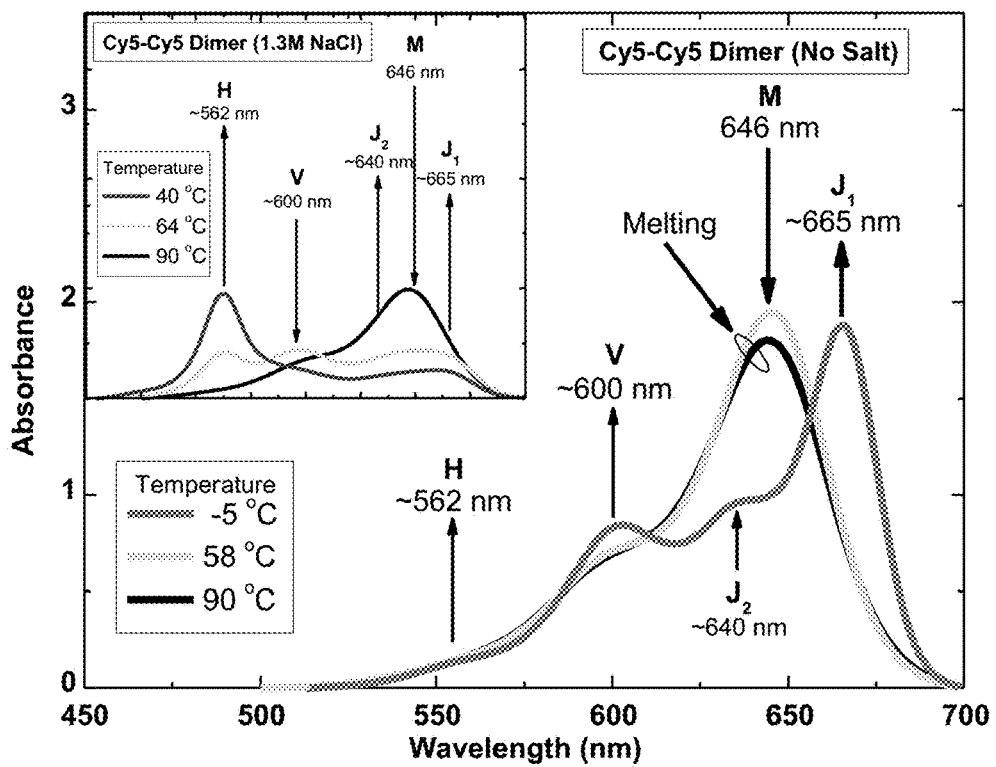
FIG. 3C is a graphical representation of changes to salt concentration, absorbance with changes in temperature.
Figure 3D:
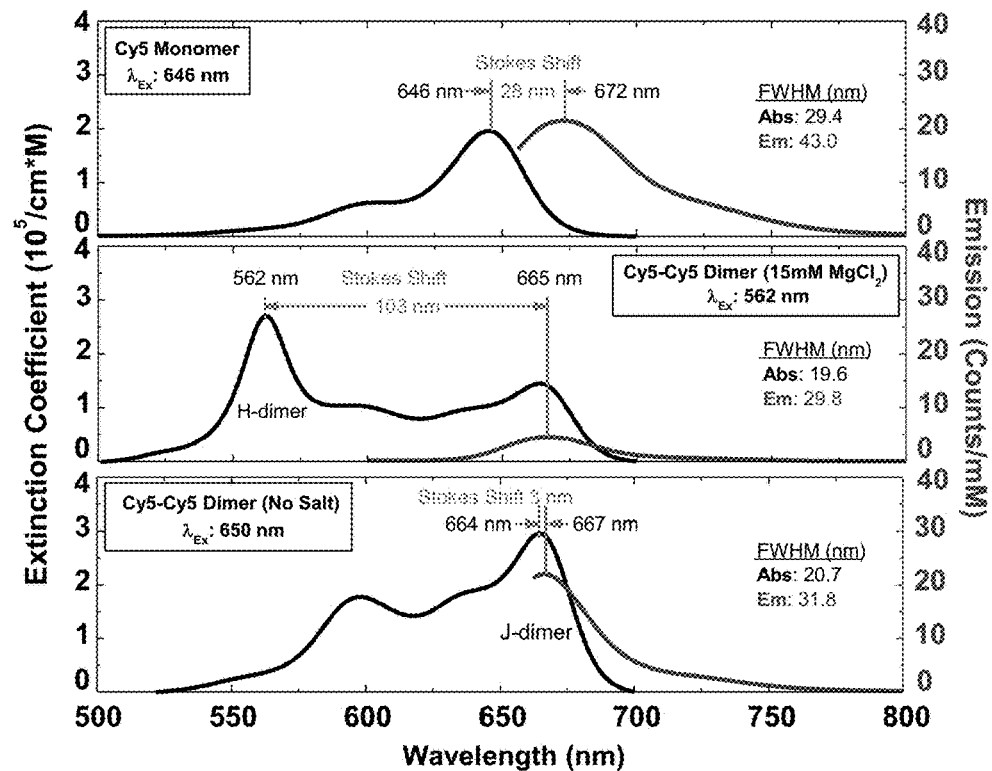
FIG. 3D is a graphical representation of emission with changes to salt.

The orientation on a linear oligomer, which affects the absorbance spectra, is also affected by characteristics of the solution, including salt concentration (FIG. 3A), temperature (FIG. 3C), and cation concentration. Therefore, by altering the conditions of the solution, it is possible to fine tune the absorbance spectra multiple chromophores nano-spaced from each other. As shown in FIGS. 3A and 3B, as the salt concentration increases, a chromophore dimer may be fine-tuned to exhibit either J-dimer characteristics at lower salt concentrations or H-dimer characteristics at high salt concentrations. FIG. 3C further shows that by altering both the temperature and salt concentrations, it is further possible to tune the chromophores for specific characteristics. FIG. 3D shows that not only the absorbance, but the emission is altered by changing the concentration of salt in the solution.

Figure 4A:
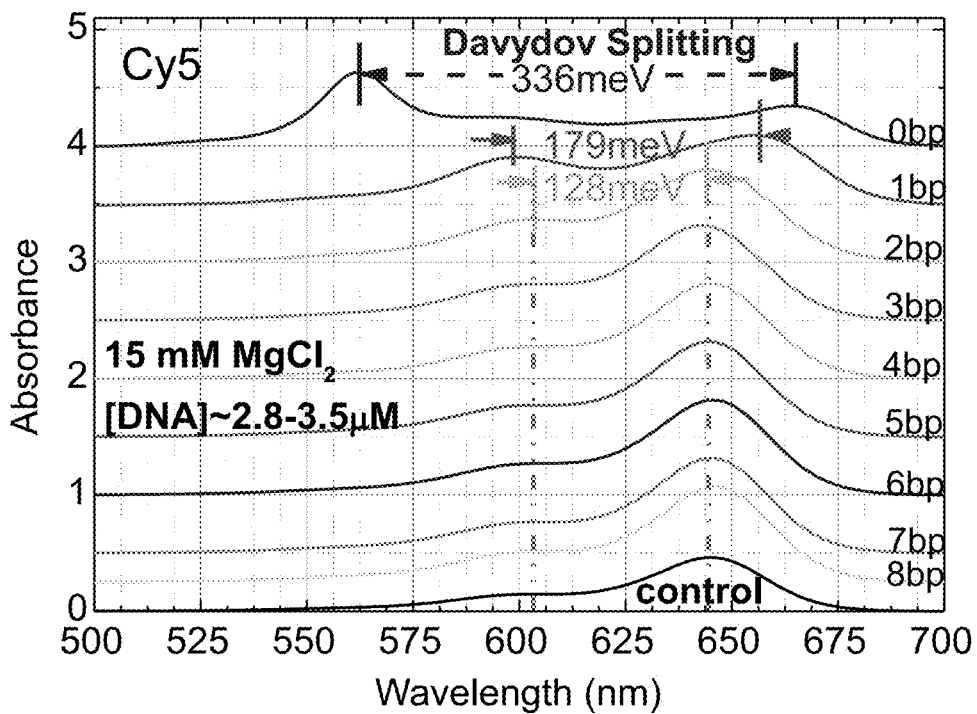
FIG. 4A is a graphical representation of the changes in absorbance verses wavelength as a function of Cy5 dimer separation examined by varying the number of nucleotides between monomers.
Figure 4B:
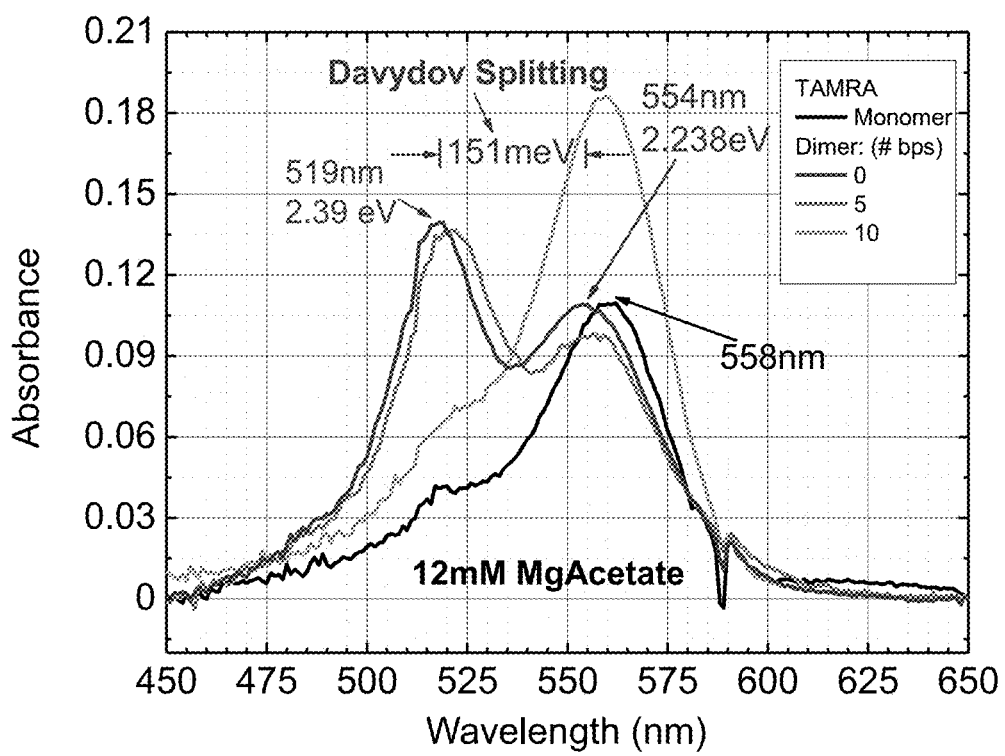
FIG. 4B is a graphical representation of the changes in absorbance verses wavelength as a function of TAMRA dimer separation examined by varying the number of nucleotides between monomers.

Additionally, the absorbance spectrum of the two chromophores on a linear oligomer is also affected by the nanospacing of two chromophores. As the distance increases, the Davydov splitting disappears and the absorbance spectrum approaches that of the monomer (FIGS. 4A and 4B). As shown in FIGS. 4A and 4B, as two chromophores are moved apart, the Davydov splitting seen when the chromophores are within sufficiently close from each other disappears. Further, as shown by FIGS. 4A and 4B the distance in which the Davydov splitting is lost is different for different chromophores.

Taken together, by altering the composition of the solution surrounding the nucleotide architecture and by altering the distance between the chromophores, one skilled in the art may alter the absorbance and emission spectra for two or more chromophores bound to a nucleotide architecture to fine tune toward dimer type.

Figure 5:
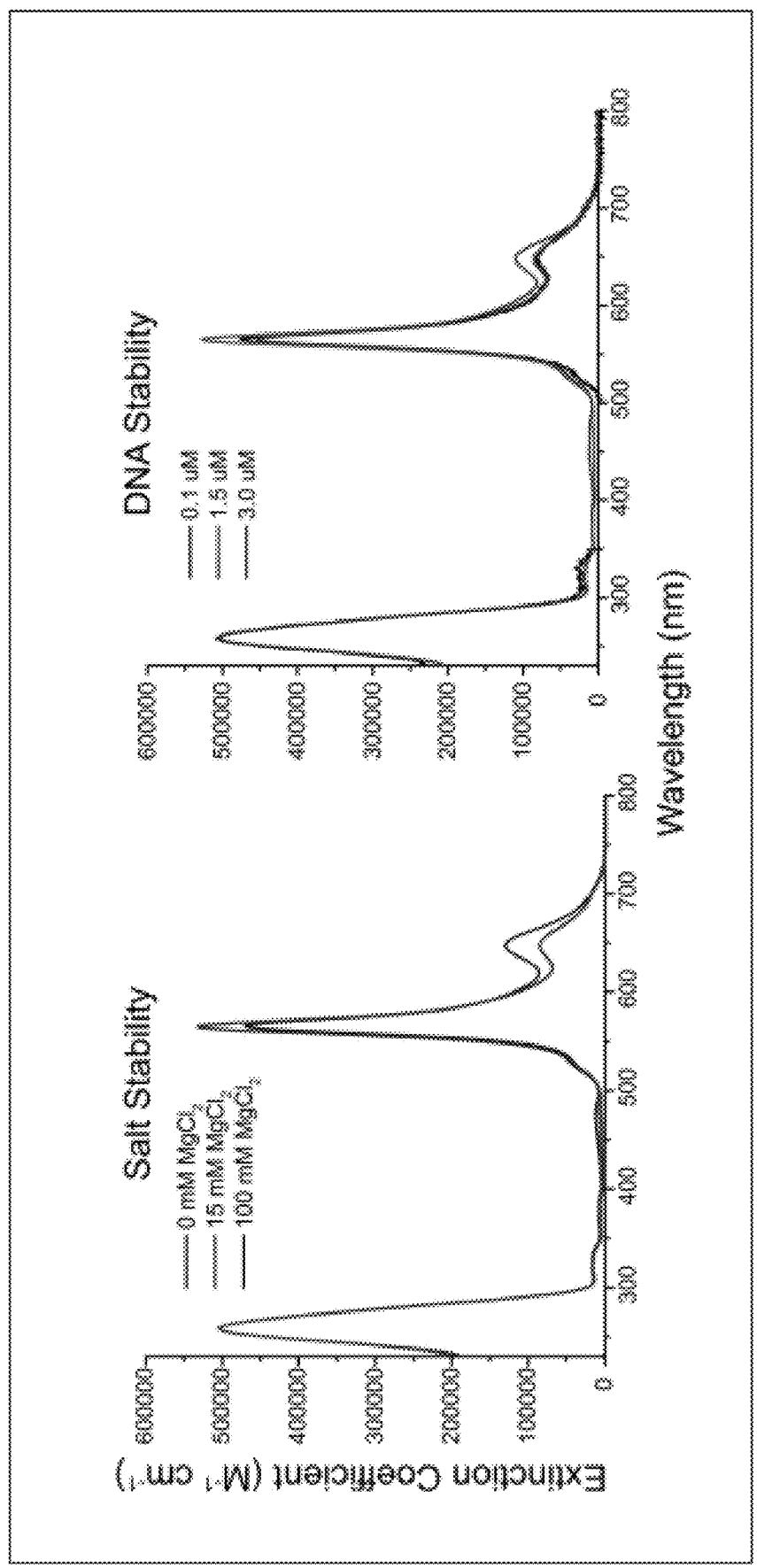
FIG. 5 is a graphical representation of the stability of a chromophore tetramer attached to an immobile 4-arm junction template in varying amounts of salt or DNA concentration.
Figure 6A:
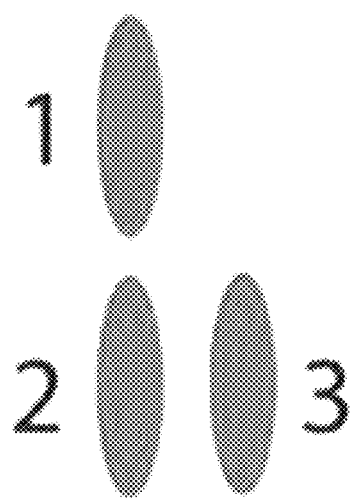
FIG. 6A is a schematic representation of a chromophore trimer arranged in an "L" configuration such that chromophores 1 and 2 couple in a J-dimer configuration and chromophores 2 and 3 couple in a H-dimer configuration.
Figure 6B:
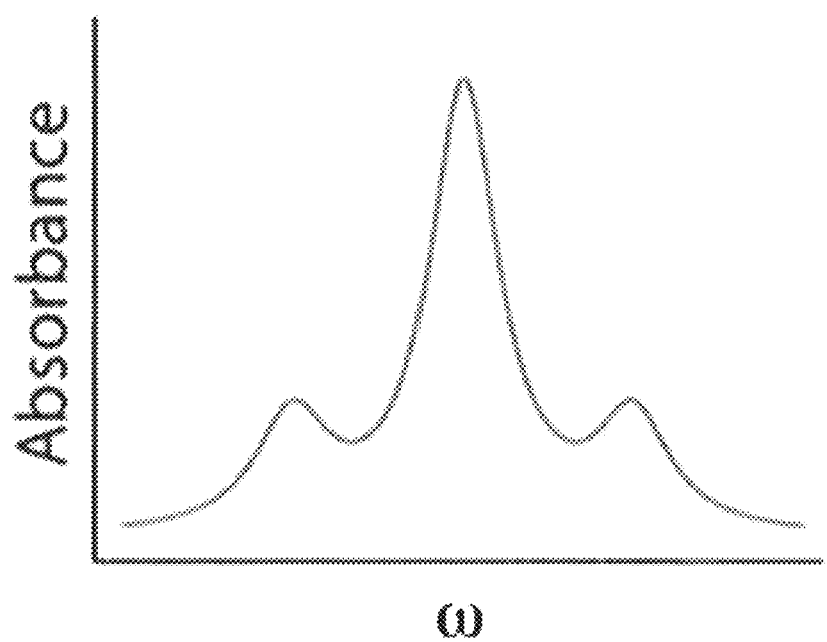
FIG. 6B is a graphical representation of the absorbance spectrum for the timer.

When more rigid nucleotide structures are used, such as but not limited to Holiday Junctions, the architecture is more capable of holding the chromophores in a rigid position, losing the flexibility seen in the linear strands (FIG. 5).

In an embodiment two chromophore dipoles are held by an architecture nanospaced head to tail to form a J-dimer. In another embodiment two chromophore dipoles are held by an architecture in parallel nanospaced to form a H-dimer. In another embodiment two chromophore dipoles are held oblique to each other by an architecture to form a mixed J/H-dimer.

In another embodiment, three chromophores are positioned within the architecture so that two of the three chromophores form a J-dimer, and two of the three chromophores form a H-dimer. In a different embodiment, the chromophores are positioned such that two form a J-dimer and the third forms two mixed J/H-dimers. In yet another embodiment, two of the chromophores form a H-dimer and the third forms two mixed J/H-dimers.

In yet another embodiment, a tetramer of chromophores are positioned within the architecture such that two H-dimers, two J-dimers are formed, and two mixed J/H-dimers form. In other embodiments, the tetramer can be position so that two H-dimers and four mixed J/H-dimers are formed. In yet another embodiment, the tetramer is positioned so that two J-dimers and four mixed J/H-dimers are formed.

In some embodiments, the chromophores all have the same optical transition energies. In other embodiments, the chromophores differ in their optical transition energies. The different optical transition energies allow the construction of a set phase shifter having desired values of absorbance and emittance.

In other embodiments, the basic configurations dimer, trimers, and tetramers as described above can be joined with other monomers, dimer, trimers, and tetramers in order to form more complex structures with desired dimer types.

Wires, Circuits, Gates, and Quantum Computing

Quantum algorithms enable the speed-up of computation tasks such as, but not limited to, factoring and sorting. These computations may be performed by an excitonic quantum computer. The excitonic quantum computer combining the more complex chromophore structures, as discussed above, can be made into exciton coherence wires, circuits, and gates. Wires may be formed when a series of chromophores are held within the architecture so that when a first chromophore, the "input chromophore," is excited and emits an exciton, the exciton passes, without loss of energy if sufficiently close, to a second chromophore. That chromophore may then pass the exciton to a third chromophore, and so on down a line of chromophores in a wave like manner. The wires may be straight or branched and may be shaped to go in any direction within the architecture. The architecture may contain one or more wires. Depending on the architecture system used, the wires may be formed along a single nucleotide brick, such as in using the scaffold strand of nucleotide origami, or multiple bricks may comprise the wire, such as in molecular canvases.

Figure 7A:
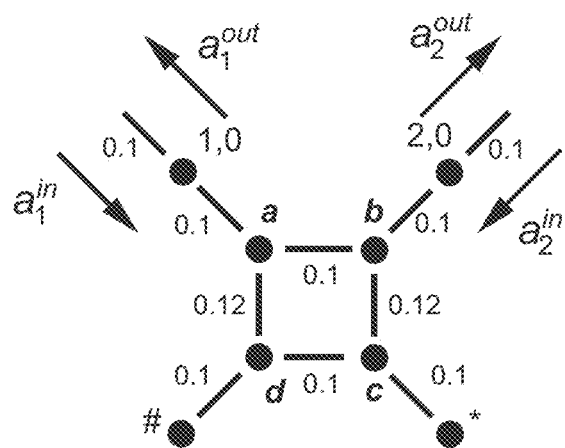
FIG. 7A is a schematic representation of a phase gate, which helps form the basis of quantum computing.
Figure 7B:
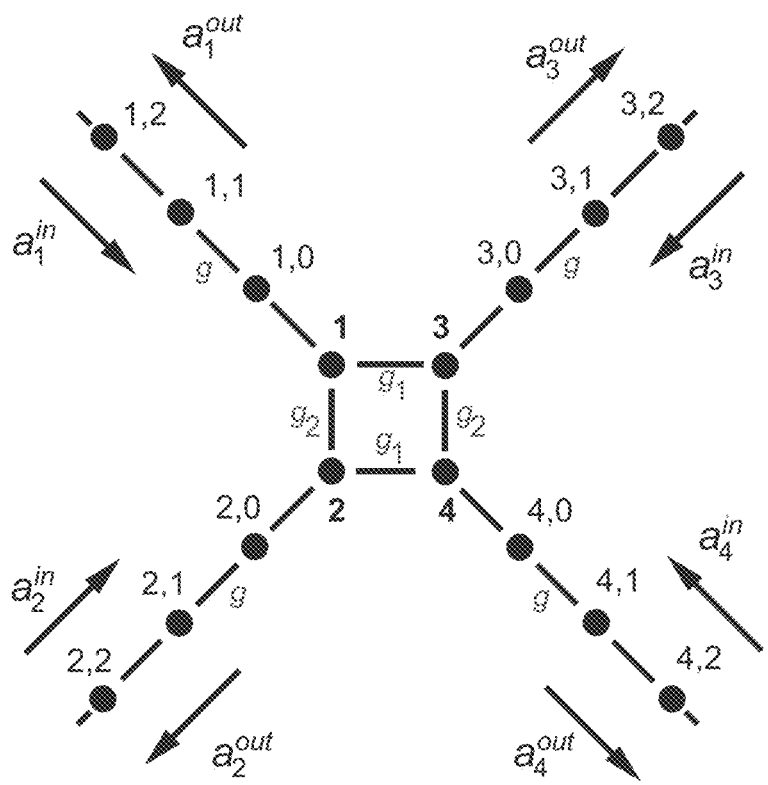
FIG. 7B is a schematic representation of a basis-changing gate which elps form the bases of quantum computing.

When two or more wires are brought sufficiently close to each other such that they are nanospaced, the exciton may transfer from one wire to the other. By controlling this transfer, it is possible to build quantum circuits and gates. Two basic gates are needed for universal quantum computing: basis-change gates (FIG. 7B) and phase-shift gates (FIG. 7A). The basis-change gate function as a signal divider in classical computer. As the exciton propagates down one wire and if another wire is sufficient close, the exciton will delocalize and enter a superposition state where it resides on both wires.

The phase-shift gate alters the excitons phase by controlling the distance the exciton travels along the two wires. As shown in FIG. 7A, they may be done by first bringing two wires within nanospace from each other and then bending one or more wire away from the other in order to create two different lengths of the wires before bringing the wires close again.

Figure 7C:
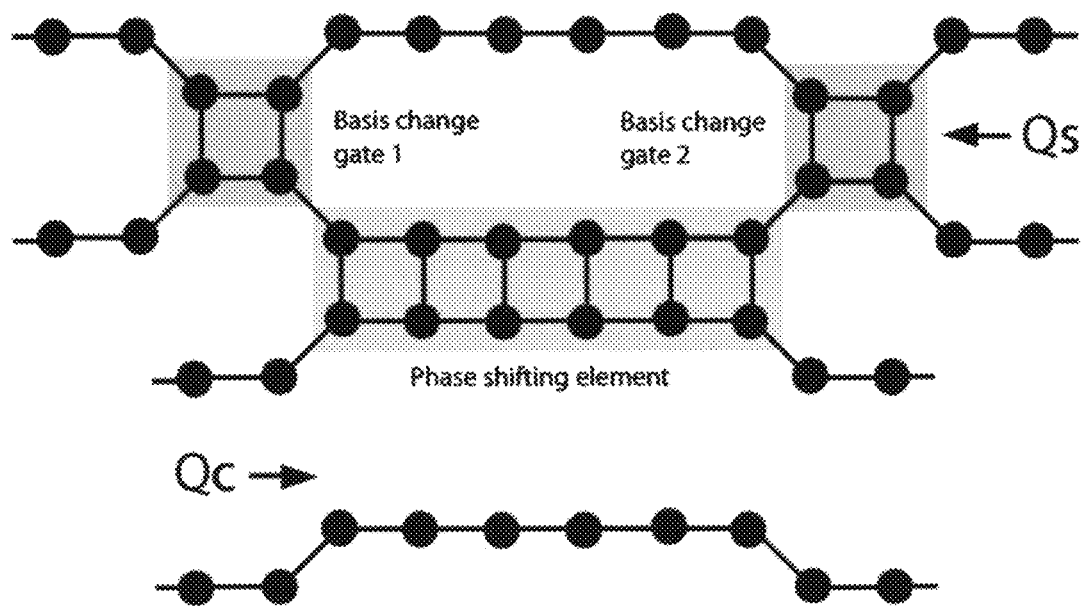
FIG. 7C is a schematic representation of a controlled basis change gate. The dots represent the chromophores.

However, with just these two types of gates, quantum computing does not outperform classical computing. A third kind of gate, the controlled basis-change gate (FIG. 7C) enables the entanglement of many-exciton states so that a network of quantum gates as if it is performing many different computations simultaneously. An exemplary controlled basis-change gate may be made from two basis-change gates and a phase-shift gate, with the phase-shift gate between the two basis-change gates. The controlled basis-change gate relies on the interaction between two excitons. When two excitons reside on neighboring chromophores they feel each other's presence just like two electrons will feel each other's Coulomb repulsion when they are brought close together. The two exciton interaction arises from static Coulomb interactions between molecules and is strong when the molecules have an asymmetric molecular structure than those with a symmetrical molecular structure. Asymmetric molecules possess a permanent electric dipole which changes sign when the molecule is excited from the ground state to the excited state. The static Coulomb interaction, in this case is a dipole-dipole interaction which, when both chromophores are excited (the two exciton case), differs in sign from the case when only one chromophore is excited (the one exciton case). Due to the static Coulomb interactions between chromophores one exciton will accumulate extra phase in the presence of the other exciton. As a result, the presence or absence of one exciton can control of the other exciton moves through a basis change gate.

Additionally, additional gates may be incorporated into the architecture, such as, but not limited to, Hadamard gates, momentum switches, and Cθ gates (see Childs et al., *Universal Computation by Multiparticle Quantum Walk*, Science, 339, 791-94 (2013), herein incorporated by reference).

Using the DNA architecture to control the positioning of the chromophores and the wide range of chromophores with different optical transition energies, the phase-shift gates can be controlled to only have a finite set of phase angles. By controlling the position and optical transition energies of the various gates, a set of gates, or a quantum circuit.

The wires, gates, and switches as discussed above can be joined together to answer questions that benefit from quantum algorithms such as, but not limited to, sorting, factoring, and database searching. To initialize the system, input chromophores are excited by using the light with the proper wavelength and polarization in such a manner that only the desired subset of chromophores is excited when the system is hit with an initializing pulse of light. The wavelength and degree of polarization of the light may match that of input chromophores in order to excite the chromophores and cause exciton emission. Any light source that may produce the wavelength used by the chromophore may be used, such as, but not limited to, lasers, including ultra-fast lasers.

After initializing, the excitons then propagate from chromophore to chromophore along the wires into the various gates. The various gates than calculate the answer, such as a sorted list or mathematical problem. The output, or readout, can be done by using fluorescent reporter dyes to which the answer of the quantum computation is delivered by ordinary FRET. While this would be particularly beneficial for problems in which the output has a limited number of bits, these problems have applications in aeronautics, Earth and space sciences, and space exploration, among other fields of research. Additionally, these systems because it demonstrates that quantum coherence is observed at room temperature in a wet and noisy environment, an environment that is normally hostile to quantum coherence.

In an embodiment, the chromophore bound nucleotide architecture forms a single gate or switch. In other embodiments, the chromophore bound nucleotide architecture forms multiple gates and/or switches.

In other embodiments, multiple chromophore bound nucleotide architectures, each comprising of one or more gate and/or switch, are aligned to form more complex circuits. The aligned architectures may be aligned using light or exciton wires to move the result of a quantum computation from one architecture to another. In a further embodiment, the multiple architectures may be aligned by placement upon a breadboard. Using this alignment allows to the output of one architecture to provide the input for a second architecture along the complex circuit.

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

In order to determine the position of a Cy5-Cy5 dimer bound to a nucleic acid oligomer, the absorbance and energy were measured over a range of wavelengths, covering the known absorbance and emittance wavelengths of Cy5, ranging from about 500 nm to about 6200 nm and compared to a Cy5 monomer.

The absorbance verses energy of a Cy5 monomer attached to a linear single stranded DNA oligomer (ssDNA-Cy5) was compared to Cy5-Cy5 dimer attached to a double stranded DNA oligomer (dsDNA-Cy5) in the presence of 15 mM $MgCl_2$. The concentration of DNA was about 3 µM. The monomer and dimer were exposed to increasing wavelengths of light and the absorbance and energy was measured.

Figure 2A:
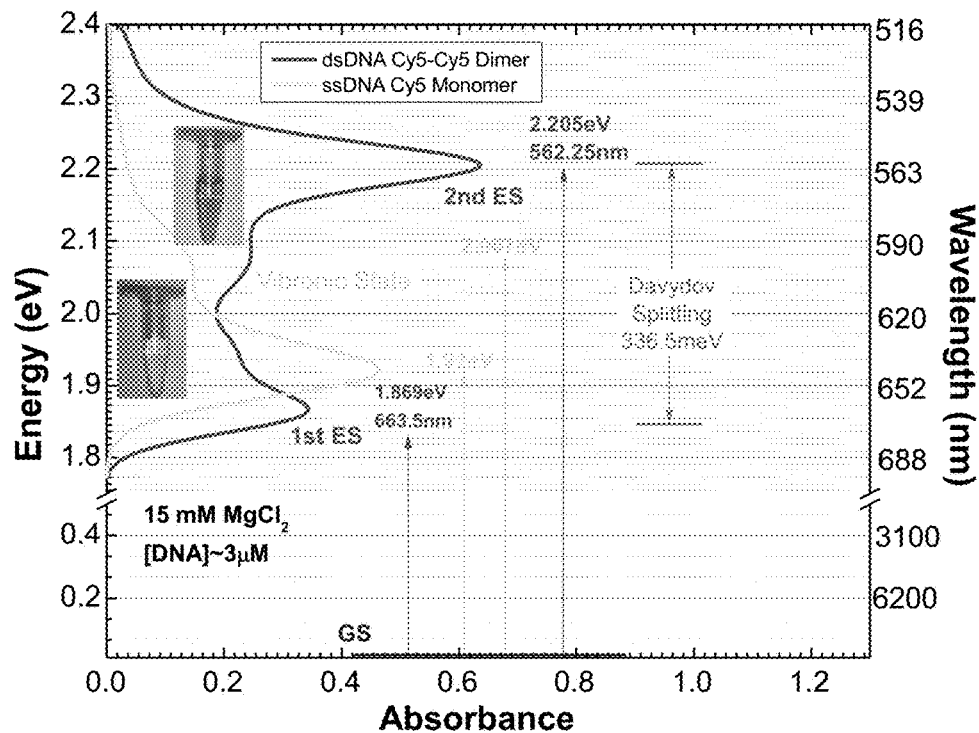
FIG. 2A is a graphical representation of the absorbance versus energy of (i) Cy5 chromophore covalently attached to a single stranded DNA (ssDNA-Cy5) monomer with one primary exciton absorption peak; (ii) a Cy5-Cy5 dimer on double stranded DNA (dsDNA-Cy5 dimer) showing Davydov splitting causing two exciton absorption peaks: $1^{st}$ excited state (ES) at 1.87 eV from ground state (GS) shows J-Dimer characteristics due to the red shift from the monomer; $2^{nd}$ ES at 2.205 eV shows H-Dimer characteristics due to the shift from the monomer. Davydov splitting shows the Cy5 pairs are at oblique angles. Taken in typical room light conditions, the micrographs show the Davydov splitting causes visible color change to the unaided eye. The micrograph also shows observations consistent with exchange narrowing.

As shown in FIG. 2A, the monomer has one primary absorption peat at 1.92 eV. In comparison, the dimer showed Davydov splitting, having two exciton absorption peaks, one at 1.87 eV and one at 2.205 eV. The 1.87 eV peak, a red shift from the monomer peak, shows the presence of J-dimer behavior. The 2.205 eV peak, a blue shift from the monomer peak, shows the presence of H-dimer behavior. As shown in the micrograph, this split causes a visible color change to the unaided eye. FIG. 2A also shows the presence of exchange narrowing, as the two peaks of the dimer show a narrower excitation range than the monomer.

Figure 2B:
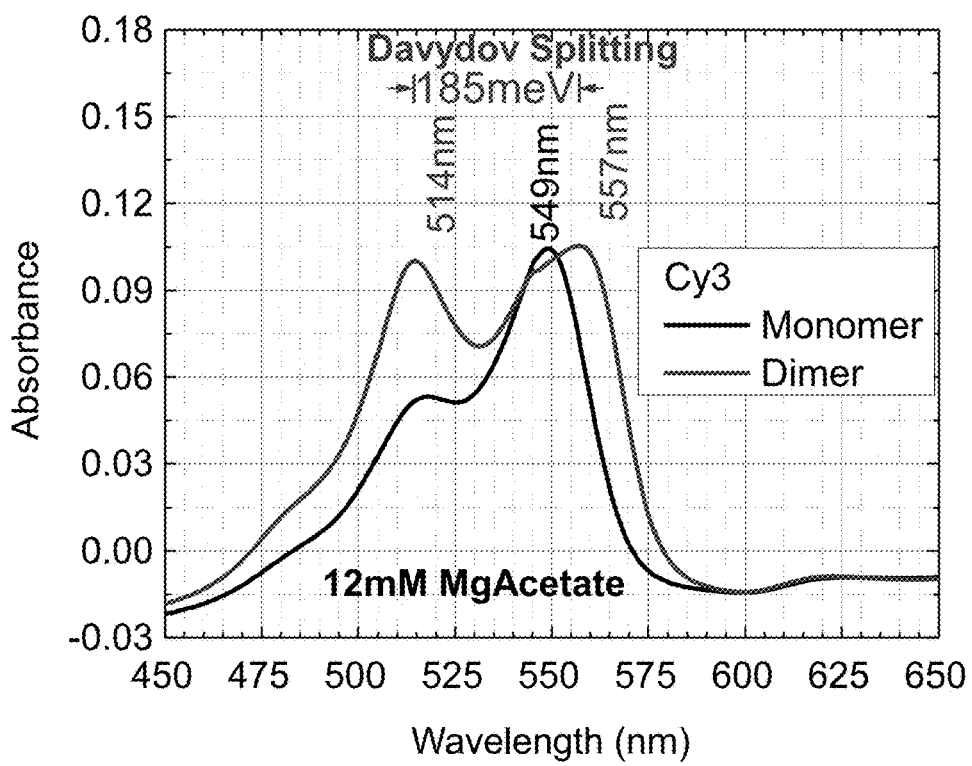
FIG. 2B is a graphical representation of the Cy3 dimer absorbance at different wavelengths compared to the Cy3 monomer.

Cy3 dimers were also compared to Cy3 monomers (FIG. 2B). Both the dimer and the monomer were exposed to about 450 nm to about 650 nm light and the absorbance was measured. The Cy3 dimer, like the Cy5 dimer, showed a Davydov shift, having characteristics of both J-dimers and H-dimers.

Due to the presence of the Davydov splitting, showing both a red and blue shift when compared to the monomer, the orientation of the chromophores on the dsDNA-Cy5 can be determined to be at an oblique angle to each other. The oblique position of chromophore dipoles allows for the two different energy states because the other dimers, J-dimers and H-dimers do not permit the two excited energy states.

Example 2

To measure the flexibility of the dsDNA-Cy5 on a linear strand of nucleic acid, the conditions of the solution and temperature were altered to detect changes in the absorbance spectrum.

The linear dsDNA-Cy5 strands were exposed to wavelengths of about 500 to about 700 nm. The salt concentrations were altered from 0 to about 1500 mM of NaCl. As shown in FIG. 3A, as the concentration of salt increased, dsDNA-Cy5 showed a reduction in Davydov splitting ($J_1$-V peaks), and a loss of J-dimer characteristics ($J_1$ peak). At about 1000 mM NaCl, dsDNA-Cy5 showed a loss of J-dimer characteristics, with a result of just H-dimer characteristics when compared to the ssDNA-Cy5 monomer. As shown in FIG. 3B, an increase in salt levels from 0 to about 909 mM NaCl showed the CD changed as well, with 0 mM salt showing Davydov splitting and J-dimer characteristics and 909 nM NaCl showing H-dimer characteristics. The change in CD shows that polarization and angle of the chromophore may also be optimized. This is important for stimulating specific chromophores, such as input chromophores, for quantum computing.

Changing both the salt concentrations and temperature also showed a change in absorbance verses wavelength of the dsDNA-Cy5 in a solution of 1× TAE buffer (FIG. 3C). The dsDNA-Cy5 composition was also compared to the ssDNA-Cy5 composition. When comparing no salt with 4.8 µM DNA compared to 1.3 M NaCl with 4.3 µM DNA a strong J-dimer peak appears without an H-dimer in the no salt whereas the 1.3 M NaCl shows a strong H-dimer peak without a J-dimer peak. Exchange narrowing, compared to the monomer peak, is evident for both the J-dimer and the H-dimer. Temperature changes also showed an effect as it got closer to the melting temperature for the double stranded DNA. As the temperature increased, both the J-dimer (with no salt) and the H-dimer (with 1.3 M NaCl) resulted in absorbance spectra more similar to the monomer.

The Stokes Shift was also affected by a change in salt concentration. As shown in FIG. 3D, at 15 mM $MgCl_2$ the Stokes Shift increased from 28 nm, the Stokes Shift of the Cy5 monomer, increases to 103 nm due to the red shift of the H-dimer lowers the Extinction Coefficient. At no salt, in the presence of the J-dimer, the Stokes Shift narrowed to 3 nm.

Due to the flexibility of the dsDNA-Cy5, it is possible for one skilled in the art to use salt and temperature to fine tune the orientation on a linear oligomer.

Example 3

To determine the effect of separation on the absorbance spectrum, the number of nucleotides to which the chromophores were bound along a linear oligomer were varied for different dyes.

As shown in in FIG. 4A, two Cy5 chromophores were bound from 0 to 8 nucleotides apart on a double stranded DNA oligomer and keeping the salt concentration of the solution at 15 mM $MgCl_2$. As shown, as the distance increased the absorbance spectrum of the Cy5 chromophores exhibited dimer characteristics, as evidenced by the Davydov splitting, at close distances of about 2 nucleotides (bp) or less. At 3 nucleotides and more the Cy5 chromophores exhibited monomer characteristics. In contrast, TAMRA chromophores in a 12 mM MgAcetate solution showed dimer characteristics when spaced further apart from each other, maintaining dimer characteristics at least until 5 nucleotides apart (FIG. 4B). The dimerization characteristics for TAMRA was lost at 10 nucleotides as measured by the change in absorbance spectrum.

Therefore, to maintain dimer characteristics, the individual chromophore molecules must remain near each other or they will act like monomers.

Example 4

To measure the effect of using more complicated and rigid architectures on chromophore behavior, the chromophores were bonded to an immobile four arm-junction architecture (4AJ, i.e. Holliday junction) (see Cannon et al., *Large Davydov Splitting and Strong Fluorescence Suppression: An Investigation of Exciton Delocalization in DNA-Templated Holliday Junction Dye Aggregates*, 2018, J. Phys. Chem. A, doi:10.1021/acs.jpca.7b12668, Supplemental Information, herein incorporated by reference), while the salt and DNA concentration in the solution were varied.

As shown in FIG. 5, as the salt concentration increases from 0 to 15 to 100 mM $MgCl_2$, there is no change in the extinction coefficient over wavelengths ranging from 0 to about 800 nm. Similarly, as the DNA concentration increased from 0.1 to 1.5 to 3.0 µM, there was also no change in the extinction coefficient over the same range of wavelengths.

Therefore, in contrast to a linear strand of DNA which may be tuned using salt concentrations, a more rigid architecture can more securely fix a chromophore in place, stabilizing the chromophores. This would allow one skilled in the art to select either a rigid or flexible system, or a combination thereof, to better form quantum wires and circuits of the desired shapes and absorbance spectra.

Example 5

Figure 8A:
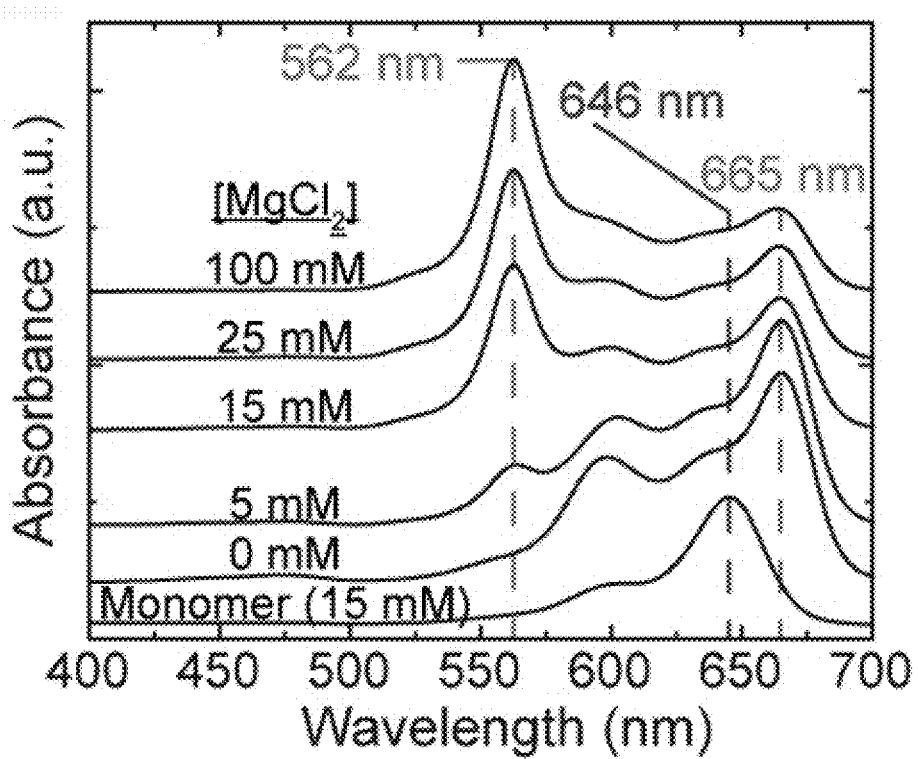
FIG. 8A is a graphical representation of the absorbance spectra of Cy5 J-dimers and/or H-tetramers bound to a mobile 4-arm junction template with varied $MgCl_2$ with a constant DNA concentration.
Figure 8B:
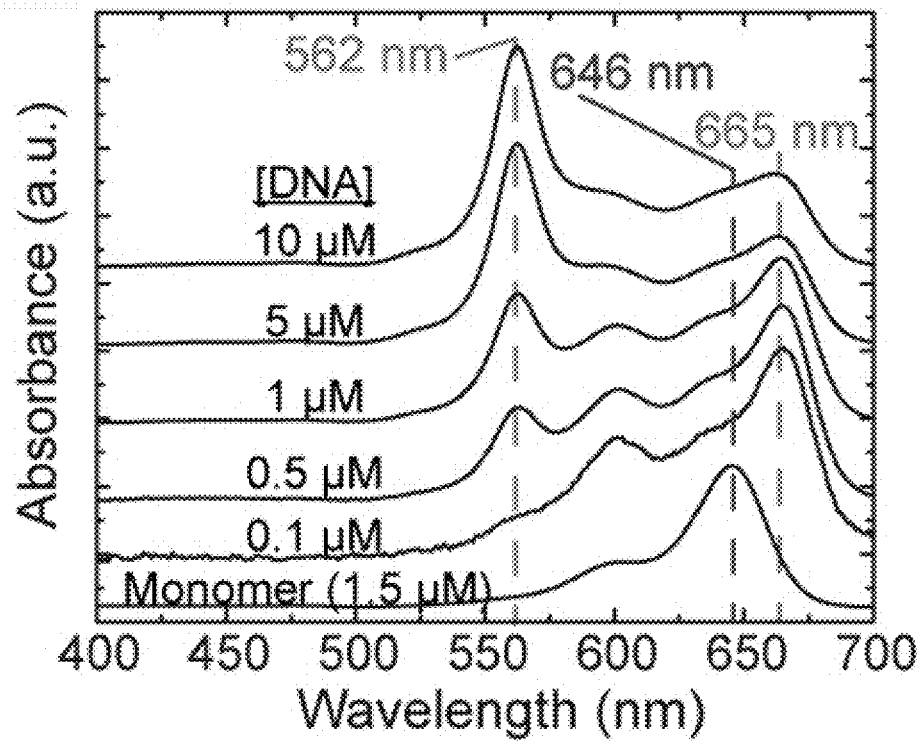
FIG. 8B is a graphical representation of the absorbance spectra of Cy5 J-dimers and/or H-tetramers bound to a mobile 4-arm junction template with varied DNA with a constant $MgCl_2$ concentration.
Figure 9A:
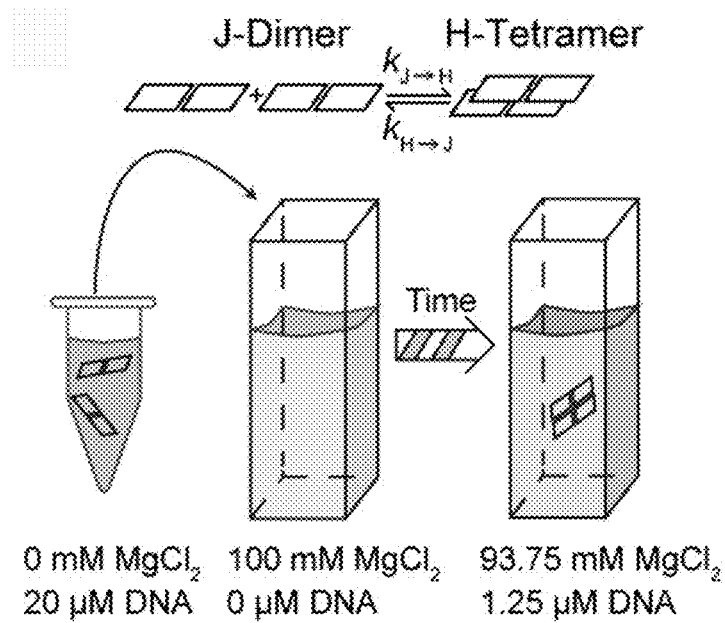
FIG. 9A is a schematic representation of the changes of J-dimers in a low salt concentration solution into H-tetramers in a high salt solution on mobile 4-arm junction over time due to four-way branch migration.
Figure 9B:
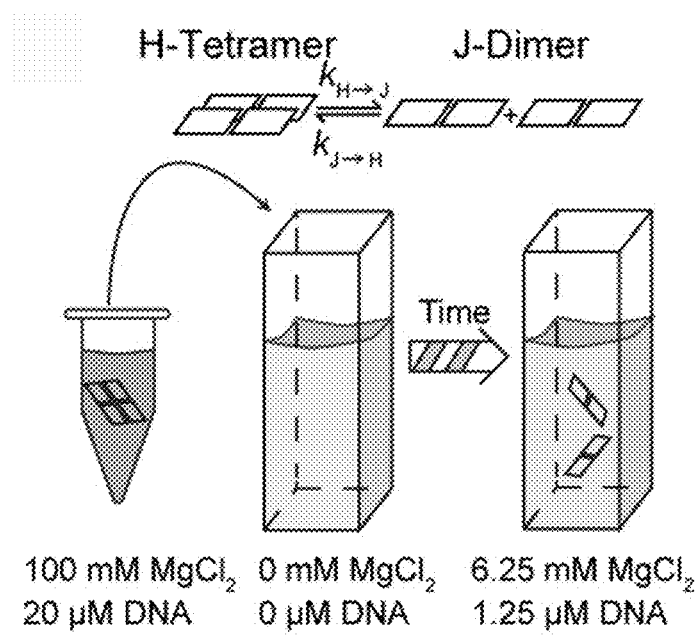
FIG. 9B is a schematic representation of the changes of H-tetramers in a high salt solution into J-dimers in a solution without salt over time due to disassociation of the complement sequences of the mobile 4-arm junction.

To further characterize environmental effect on more complex structures of a mobile nucleotide template, Cy5 chromophores were attached to four different ssDNA strands (see Cannon et al., *Coherent Exciton Delocalization in a Two-State DNA-Templated Dye Aggregate System*, 2017, J. Phys. Chem. A, 121:6905-6916, Supplemental Information, herein incorporated by reference) and solution salt and DNA concentrations were varied. The four different ssDNA strands were designed to allow two complement ssDNA strands to form two dsDNA strands. The two dsDNA strands may then undergo four-way branch migration to form a 4AJ template. The complementary ssDNA strands were first annealed to position the Cy5 chromophores into a J-dimer. The Cy5 chromophore were further positioned such that if the two dsDNA strands form the 4AJ template, the resulting Cy5 tetramer would form H-dimers. The two dsDNA strands were then mixed at various salt (0-100 mM added MgCl2; DNA held constant at 1.5 µM) and DNA (0.1-10 µM; salt held constant at 15 mM) concentrations. The absorbance spectrum of each sample (FIGS. 8A and 8B) at various salt and DNA concentrations was measured. FIGS. 8A and 8B shows that with changes in salt or DNA concentration the locations of the absorbance peaks remain constant within the selected $MgCl_2$ and DNA concentration ranges, respectively.

The absence of variation in the position of the absorption peaks shows that the relative orientations between the two dyes are constant for the two populations, showing that the dyes do not continuously rearrange their configuration as a function of salt concentration or DNA concentration but instead exist in one of two geometrically distinct states, as a J-dimer (duplex) or an H-tetramer (4AJ). Accordingly, the relative concentration of each aggregate state varies with salt concentration and/or DNA concentration as indicated by the change in relative peak intensities for the J-dimer ($\lambda_{max}$=665 nm) and the H-tetramer ($\lambda_{max}$=562 nm). The increase of intensity at 562 nm for both the increase in salt and DNA show that at higher concentrations of both salt and DNA, the H-tetramer is favored over the J-dimers (FIGS. 8A, 8B, 9A, and 9B). Thus, the observed spectra are a manifestation of spectral overlap between J- and H-aggregates.

This shows that the intensity of absorbance may be controlled of mobile templates by altering the salt and/or DNA concentrations. This further shows that depending on the rigidity of the DNA architecture, salt and/or DNA concentrations may be altered in order to fine tune the absorbance.

What is claimed is:

1. A nucleotide brick molecular canvas used for quantum computing, comprising:
   at least one nucleotide brick; and
   at least two chromophores, wherein said at least two chromophores are bound to the at least one nucleotide brick, and wherein said at least two chromophores are nanospaced from each other;
   wherein the at least two chromophores comprise at least two asymmetric molecules, each of the asymmetric molecules comprising a permanent electric dipole which changes sign when the each of the asymmetric molecules are excited from the ground state to the excited state.

2. The nucleotide brick molecular canvas of claim 1, wherein the canvas comprises between 1 and about 5,000 bricks.

3. The nucleotide brick molecular canvas of claim 1, wherein the at least one nucleotide brick comprises one or more of RNA, DNA, LNA, PNA, and/or UNA and is about 24 to about 42 nucleotides in length.

4. The nucleotide brick molecular canvas of claim 1, wherein said at least one of the at least two chromophores is one or more of: 6-FAM, 6-FAM (Fluorescein), Fluorescein dT, Cy3, TAMRA, JOE, Cy5, MAX, TET, Cy5.5, ROX, TYE 563, Yakima Yellow, HEX, TEX 615, TYE 665, TYE 705, Alexa Fluor 488, 532, 546, 647, 660, 750, 5' IRDye 700, 800, and 800CW, Rho101, 590, 633, 647N, Rhodamine Green-X, Rhodamine Red-X, and 5-TAMRA, WellRED D4, D3, and D2, 6-FAM, Fluorescein, Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, and/or -601XL.

5. The nucleotide brick molecular canvas of claim 1, wherein, in addition to said at least two chromophores, the nucleotide brick molecular canvas further comprises at least one symmetric molecule.

6. The nucleotide brick molecular canvas of claim 1, wherein said nucleotide brick molecular canvas further comprises one or more of one-, two-, and/or three-dimensional sections.

7. The nucleotide brick molecular canvas of claim 1, wherein the at least two chromophores are covalently bound to the bricks.

8. The nucleotide brick molecular canvas of claim 1, wherein at least one of the at least two chromophores is covalently bound to a linker nucleotide oligomer and wherein said linker nucleotide oligomer Watson-Crick pairs with a brick within the nucleotide brick molecular canvas.

9. The nucleotide brick molecular canvas of claim 1, wherein said nucleotide brick molecular canvas further comprises exciton gates and/or exciton switches.

10. A complex quantum circuit for quantum computing, comprising:
at least two nucleotide brick molecular canvases of claim 1, wherein a first nucleotide brick molecular canvas is aligned to a second nucleotide brick molecular canvas, and wherein an output chromophore of said first nucleotide brick molecular canvas is spaced close enough to an input chromophore of said second nucleotide brick molecular canvas such that the output chromophore can pass an exciton to the input chromophore.

11. The complex quantum circuit for quantum computing of claim 10, wherein said at least two canvases each comprise between 1 and about 5,000 bricks.

12. The complex quantum circuit for quantum computing of claim 10, wherein the bricks comprise one or more of RNA, DNA, LNA, PNA, and/or UNA and are about 24 to about 42 nucleotides in length.

13. The complex quantum circuit for quantum computing of claim 10, wherein at least one of the at least two chromophores is one or more of: 6-FAM, 6-FAM (Fluorescein), Fluorescein dT, Cy3, TAMRA, JOE, Cy5, MAX, TET, Cy5.5, ROX, TYE 563, Yakima Yellow, HEX, TEX 615, TYE 665, TYE 705, Alexa Fluor 488, 532, 546, 647, 660, 750, 5' IRDye 700, 800, and 800CW, Rho101, 590, 633, 647N, Rhodamine Green-X, Rhodamine Red-X, and 5-TAMRA, WellRED D4, D3, and D2, 6-FAM, Fluorescein, Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, and/or -601XL.

14. The complex quantum circuit for quantum computing of claim 10, wherein at least one of the at least two chromophores is asymmetrical.

15. The complex quantum circuit for quantum computing of claim 10, wherein said nucleotide brick molecular canvases further comprises one or more of one-, two-, and/or three-dimensional sections.

16. The complex quantum circuit for quantum computing of claim 10, wherein at least one of the at least two chromophores is covalently bound to the bricks.

17. The complex quantum circuit for quantum computing of claim 10, wherein at least one of the at least two chromophores is covalently bound to a linker nucleotide oligomer and wherein said linker nucleotide oligomer Watson-Crick pairs with a brick within the nucleotide brick molecular canvas.

18. The complex quantum circuit for quantum computing of claim 10, wherein said nucleotide brick molecular canvases further comprises one or more of exciton wires, exciton gates, and/or exciton switches.

19. The complex quantum circuit for quantum computing of claim 10, wherein:
the input chromophore is exposed to light, wherein said light comprises a wavelength and polarization within the absorbance range for said polarization of said input chromophore.

20. The complex quantum circuit for quantum computing of claim 19, wherein said least two nucleotide brick molecular canvases comprise between 1 and about 5,000 bricks.

21. The complex quantum circuit for quantum computing of claim 19, wherein the bricks comprise one or more of RNA, DNA, LNA, PNA, and/or UNA and are about 24 to about 42 nucleotides in length.

22. The complex quantum circuit for quantum computing of claim 19, wherein at least one of the at least two chromophores is one or more of: 6-FAM, 6-FAM (Fluorescein), Fluorescein dT, Cy3, TAMRA, JOE, Cy5, MAX, TET, Cy5.5, ROX, TYE 563, Yakima Yellow, HEX, TEX 615, TYE 665, TYE 705, Alexa Fluor 488, 532, 546, 647, 660, 750, 5' IRDye 700, 800, and 800CW, Rho101, 590, 633, 647N, Rhodamine Green-X, Rhodamine Red-X, and 5-TAMRA, WellRED D4, D3, and D2, 6-FAM, Fluorescein, Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, and/or -601XL.

23. The complex quantum circuit for quantum computing of claim 19, wherein at least one of the at least two chromophores is asymmetrical.

24. The complex quantum circuit for quantum computing of claim 19, wherein said nucleotide brick molecular canvases further comprises one or more of one-, two-, and/or three-dimensional sections.

25. The complex quantum circuit for quantum computing of claim 19, wherein at least one of the at least two chromophores is covalently bound to the bricks.

26. The complex quantum circuit for quantum computing of claim 19, wherein at least one of the at least two chromophores is covalently bound to a linker nucleotide oligomer and wherein said linker nucleotide oligomer Watson-Crick pairs with a brick within the nucleotide brick molecular canvas.

27. The complex quantum circuit for quantum computing of claim 19, wherein said nucleotide brick molecular canvas further comprises one or more of exciton wires, exciton gates, and/or exciton switches.

28. The nucleotide brick molecular canvas of claim 1, further comprising an exciton wire composition for quantum computing, said exciton wire comprising at least one nucleotide oligomer bound to the at least two chromophores.

29. The nucleotide brick molecular canvas of claim 28, wherein said at least one nucleotide oligomer self assembles.

30. The nucleotide brick molecular canvas of claim 1, wherein said at least two nanospaced chromophores are separated by about 0 to about 10 nucleotides apart.

* * * * *